United States Patent [19]

Posch

[11] 4,053,284
[45] Oct. 11, 1977

[54] CONTINUOUS FLOW APPARATUS FOR BIOLOGICAL TESTING

[75] Inventor: Nancy Ann Posch, La Crescenta, Calif.

[73] Assignee: Akzona Incorporated, Asheville, N.C.

[21] Appl. No.: 665,358

[22] Filed: Mar. 10, 1976

[51] Int. Cl.² ............... G01N 33/16; G01N 21/00; G01N 31/14
[52] U.S. Cl. .................................... 23/259; 15/302; 15/304; 23/230 B; 23/292; 134/104; 134/167 R; 195/103.5 A; 195/127; 424/1; 424/12
[58] Field of Search ............... 23/230 B, 259, 292; 424/12; 15/304

[56] References Cited

U.S. PATENT DOCUMENTS

| | | | |
|---|---|---|---|
| 3,492,396 | 1/1970 | Dalton | 424/12 |
| 3,837,376 | 9/1974 | Brown | 23/259 |
| 3,843,444 | 10/1974 | Likhite | 424/12 X |
| 3,849,830 | 11/1974 | Wagner | 15/304 X |
| 3,873,682 | 3/1975 | Ogawa | 424/12 |

Primary Examiner—Sidney Marantz
Attorney, Agent, or Firm—Robert H. Falk; Francis W. Young; Phillip M. Pippenger

[57] ABSTRACT

A test apparatus for conducting diagnostic tests on body fluids, said apparatus having (1) a reaction vessel containing immunochemical test reagents supported as on beads and (2) a washing means cooperating with the reaction vessel, said washing means supplying washing fluid for the reaction vessel. The washing means also comprises a vacuum conduit for aspirating the washing fluid out of the reaction vessel. The apparatus is applicable to hepatitis testing.

15 Claims, 6 Drawing Figures

U.S. Patent  Oct. 11, 1977  4,053,284
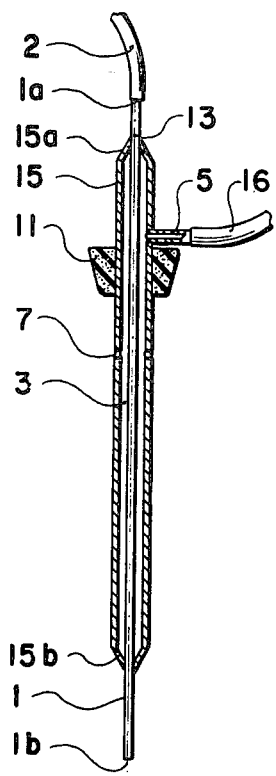
FIG. I
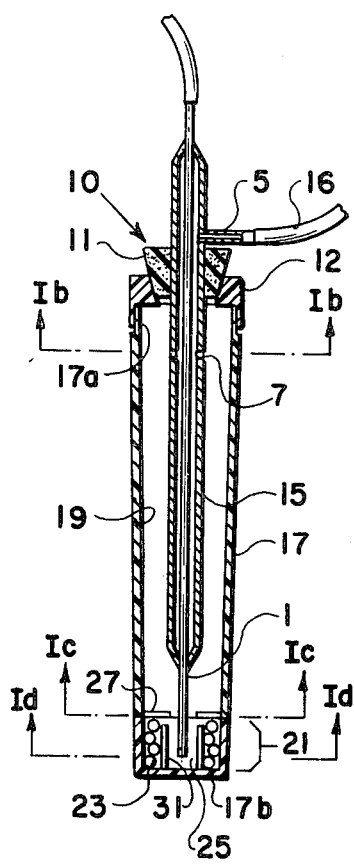
FIG. Ia
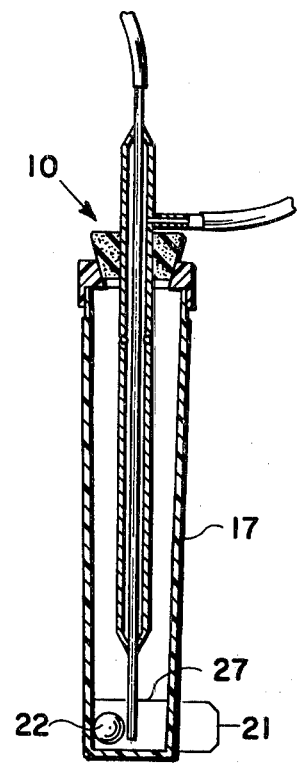
FIG. II
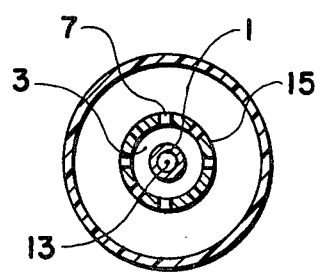
FIG. Ib
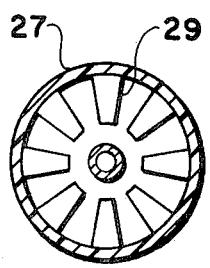
FIG. Ic
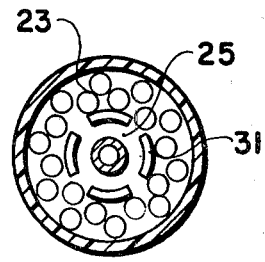
FIG. Id

CONTINUOUS FLOW APPARATUS FOR BIOLOGICAL TESTING

BACKGROUND OF THE INVENTION

This invention relates to washing apparatus and method for assaying samples of blood, urine or other body fluids for antigens or their antibodies. More particularly, this invention relates to diagnostic apparatus for a direct assay using enzymes, fluorochromes, or radio-isotopes to determine the presence of hepatitis associated antigen or it antibodies having at least two free antigenically active sites.

Although there have been methods for determining the presence of antigenically active molecules such as intact viruses, virus capsids, bacteria, hormones, haptens, etc., the known immunochemical tests require a number of discrete washing steps. For example, in testing for hepatitis associated (Hepatitis B Surface Antigen $HB_sAg$), hepatitis antibody supported on an appropriate such as a bead is contacted with an unknown serum. Following incubation, the serum must be removed from the reaction vessel by aspiration followed by inserting wash fluid and then aspirating a second time to remove the fluid. This washing step is frequently repearted five or six times and is tedious and time-consuming. The volume of wash fluid used in each discrete washing is, of course, limited by the volume of the reaction vessel. Additionally, with each aspiration step, a small volume of fluid remains behind on the sides of the vessel or in the bottom portion. When wash fluid is again added, this residue is diluted; however, on subsequent aspiration, a small portion of the diluted residue remains behind. Because of the dilution factor, it is frequently necessary to carry out the washing steps (with aspiration) five and six times to reduce the residue to levels which will not interfere with subsequent reaction steps. Additionally, as other reagents are added, it is necessary to repeat the whole washing procedure.

What is needed is a relatively quick process for washing to remove reagents from the reaction vessel. The process must also be thorough so that little, if any, residue is left behind. Presently available apparatus and methods are limited by the volume of the reaction vessel, and, because of the dilution factor mentioned above, a thorough wash will require a relatively large volume of fluid greatly in excess of the volume of the reaction vessel. Therefore, a number of discrete and time-consuming wash-aspirating steps are required.

Another problem encountered with discrete washing steps is over-flow; i.e., the clinician must be careful not to insert too much wash water. If the test tube or other apparatus overflows, surrounding test tubes or even those present in the laboratory could be contaminated. Additionally, the reaction vessel is usually open to the atmosphere giving rise to the possibility of aerosolization of highly infectious reactants.

It is the principal object of the present invention to provide diagnostic apparatus which accomplishes a quick and thorough washing in a single step without requiring a number of discrete and time-consuming wash-aspiration steps. Any desired amount of washing fluid can be employed as is necessary to achieve a thorough wash even though the fluid volume is greatly in excess of the volume of the reaction vessel.

In addition to overcoming the problems of dilution and the time-consuming washing steps, the apparatus and method also prevents aerosolization of the reagents and eliminates the problem of over-flow.

Another attractive feature of the invention is that it is relatively simple in design and easy to assembly. These features are important in making the invention available on a mass basis.

Still further objects and advantages of the diagnostic apparatus and method of the present invention will become apparent from the following description thereof and the following attached figures wherein:

FIG. I is a cut-away view of one form of washing apparatus of the present invention;

FIG. I*a* is a cut-away view of the apparatus of FIG. I in combination with a reaction vessel.

FIGS. I*b*, I*c*, and I*d* are cross-sections of the washing apparatus and reaction vessel of FIG. I*a* taken along lines I*b*, I*c*, and I*d*, respectively;

FIG. II Is a cut-away view of apparatus of FIG. I in combination with a reaction vessel containing a single large bead as the reagent support surface.

DESCRIPTION OF THE INVENTION

Briefly, the washing apparatus of the invention comprises a container fitted with a plurality of ports for introducing washing fluid into a reaction vessel during performance of a diagnostic test, and a vacuum conduit for simultaneously capturing and removing the fluid from the reaction vessel. The apparatus generally has an elongated longitudinal axis and the vacuum conduit passes through the container generally in parallel with the longitudinal axis. The container is disposed about the longitudinal axis and may be symmetrical with respect to the axis, although this feature of the invention is not critical but is helpful in achieving a uniform application of washing fluid to the interior surface of the reaction vessel.

The washing apparatus is designed for insertion into a reaction vessel to form a vacuum-tight seal. The combination of washing apparatus and reaction vessel forms a test apparatus for performing diagnostic tests on blood serum, urine, and other body fluids. The reaction vessel has a closed end and an open end which is designed to be slight broader than, and to mate in fluid-tight, vacuum sealing engagement with, the container portion of the washing apparatus following insertion into the reaction vessel. The reaction vessel has an interior surface which defines a reaction zone containing insolubilized immunochemical reagents. The insolubilized reagents are positioned on a supporting surface such as, for example, the interior surface of the reaction vessel. Alternatively, the reaction zone can contain on or more beads (plastic or glass) or similar inert geometric solids which providea suitable supporting surface. In the event that the solids are small enough to be entrained or suspended in the washing fluid, the teeth members, membrane or other material forming the forming the grid must be sufficiently fine that the solids are retained in the enclosed chamber formed in the reaction zone by the grid.

Since the apparatus functions by simultaneously introducing and removing fluid from the reaction vessel, there is a continuous flow through the reaction vessel with no accumulation. This eliminates the problem of residues which are left behind to be continuously diluted when discrete washing and aspirating steps are employed. Also, the amount of fluid (e.g., water ) employed is independent of the volume of the reaction vessel. Therefore, any amount of washing desired may be performed. Because of the simultaneous and continuous introduction and removal of fluid, as opposed to intermittent, discrete wash-removal steps, the washing operation is considerably simplified and "speeded-up" by use of the apparatus of the invention.

With reference to the embodiment of the invention depicted in FIGS. I and Ia–Id, the washing apparatus (FIG. I and indicated generally by arrow 10 in FIG. Ia) has a longitudinal axis 13 and comprises a tubular container 15 having first and second end portions, 15a and 15b, respectively, and having an interior tubular vacuum conduit 1 passing therethrough along axis 13. Container end portions 15a and 15b are closed and mate with vacuum conduit 1. Conduit 1 has first and second vents 1a and 1b, respectively. Tubular conduit 1 and container 15 share axis 13 as a common longitudinal axis and have parallel spaced-apart sides and which together an annular chamber 3 for receiving fluid. Container 15 is adapted to communicate with a source of washing fluid (not shown) through arm member 5 and tube 16, and is fitted with a plurality of ports 7 generally uniformly distributed in a band between the first and second end portions 15a and 15b of the container. Conduit 1 is adapted to communicate with a vacuum source (not shown) such as a water aspirator through the first vent 1a and tube 2 and is designed to remove fluid from the reaction vessel through vent 1b. Container 15 is fitted with an annular collar 11 which is designed to mate with reaction vessel 17 to form a vacuum seal when the test apparatus 10 is inserted into the reaction vessel. Container 15 and conduit 1 are generally metal or plastic. Collar 11 is generally made from a rubbery, air-impermeable material (e.g., rubber) to enable it to fit snugly with the reaction vessel and form an air-tight vacuum seal.

It is frequently convenient for purposes of machining the ports into the container that they be positioned in a band with each port equi-distant from the first end 15a of the container, generally closer to 15a than to 15b, and equi-distant from each other along the band. This configuration also provides a relatively uniform flow of fluid to all parts of the reaction vessel and provides a self-action to apparatus 10. However, the ports can be positioned in any configuration between the first and second ends of container 15 so long as they provide the desired fluid flow.

Apparatus 10 is designed for insertion into reaction vessel 17 as depicted in FIG. Ia to form an apparatus for performing diagnostic tests on samples of blood serum, urine, and other body fluids. Cylindrical reaction vessel 17 has a closed end 17b and an open end 17a fitted with removal cap 12 which mates with collar 11 to form an air-tight vacuum seal. The interior surface 19 of the reaction vessel defines a reaction zone 21 adjacent closed end 17b containing a plurality of polystyrene beads 23 having sheep antibody to hepatitis B surface antigen covalently bound to the surface of the beads. Reaction zone 21 also contains a well 25 defined by a grid 27 (FIG. Ia and Ib) having axial teeth 29, and by 31 extending perpendicularly to the closed end 17b of the reaction vessel. Teeth 29 and 31 form a fluid permeable barrier preventing the beads 23 from entering well 25. Other fluid permeable materials such as a membrane could be employed in place of the teeth members. The reaction vessel and beads are single-use, disposable items and are, therefore, made of plastic, although glass (preferably clear glass) can be used if desired. For the reaction vessel, the clear glass or plastic should be of sufficient quality so that reactions conducted in the vessel can be read in a spectrophotometer. Generally, beads 23 are not removed from the reaction vessel but remain in place. The reaction vessel is then analyzed to determine the extent of any diagnostic reaction. To permit analysis by colorimetric methods or by radioimmunoassay, it is preferred that the plastic in the reaction vessel be of optical quality, for example, Tyril ® brand styrene acrylonitrile copolymer or polystyrene. Where a very large area is desired, very small beads or particles can be employed in the reaction zone. In this case, the grid and/or aspirating vent 1b are sufficiently fine to prevent aspiration of the particles.

Although the apparatus of the present invention can be used with the above described reaction vessel for determining the presence of any appropriate antigen or antibody, the use of the apparatus will now be described with respect to a procedure for determining the presence of hepatitis B surface antigen ($HB_sAg$).

Where the test is to be conducted for $HB_sAg$, the beads 23 will be coated with hepatitis antibody, for example, from a human or sheep. Cap 12 is removed and human blood serum suspected of containing $HB_sAg$ is introduced into reaction vessel 17, cap 12 is replaced, and the sample is allowed to react during an incubation period with the antibody-coated beads 23. To remove residual serum which could be highly infectious, apparatus 10 is inserted into reaction vessel 17 so that collar 11 mates with cap 12 to form a vacuum-tight seal. A water aspirator or similar vacuum source is activated to pull a vacuum through vacuum conduit 1. The vacuum (causing a pressure differential washing fluid reservoir and container 15) draws water into container 15. The water is ejected through ports 7 against the interior surface 19 of the reaction vessel, flows through reaction zone 21 into well 25 and is captured by conduit 1 and removed. In passing through the reaction vessel, the water washes the interior surface 19 of the vessel and thoroughly floods the reaction zone 21 and washes beads 23. If, during this washing step, the vessel should be overturned, apparatus 10 will remain in place because of the vacuum. This safety feature is a substantial advantage in a busy laboratory where working with contagious reagents.

Following the washing step, apparatus 10 is removed from reaction vessel 17, and I-125 labelled anti-$HB_s$ is introduced into the vessel and incubated with beads 23 in reaction zone 21. Alternately, an enzyme or fluorescein can be used as the label. Following incubation, apparatus 10 is reinserted into the reaction vessel and the washing step is repeated. Apparatus 10 is then removed and the reaction vessel is placed in the well of any conventional apparatus designed to count gamma radiation. The amount of radiation is recorded and compared with the radiation levels exhibited by known positive and negative samples.

Using the apparatus of the invention in the assay method just described, a number of advantages over conventional procedures are immediately apparent. In conventional procedures, anti-$HB_s$ is positioned on a supporting surface such as a single large bead or the inner surface of a test tube. Following addition of serum and incubation with anti-$HB_s$, a syringe is used to introduce washing fluid into the test tube. The volume of fluid inserted is limited by the volume of the test tube and is generally much less than the test tube volume to minimize the possibility of splashing or overflow. The wash fluid contains diluted serum and could be very hazardous and great care must be used in conducting the test. Subsequently, an aspirating pipette is inserted to remove the fluid. This procedure is repeated three to five times. With each aspiration, a small volume of wash fluid is left behind to be diluted by the next addition of washing fluid. This procedure involving discrete wash-aspiration steps is tedious and time-consuming and is also potentially hazardous.

The apparatus of the invention continuously introduces washing fluid into reaction vessel 17 and simultaneously removes the fluid through vacuum conduit 1. This provides a continuous flow of fluid through reaction vessel 17 with no accumulation. Serum or other reagents to be removed are swept along and entrained in the flow of fluid through the reaction vessel. This eliminates the problem of residues which are left behind to be continuously diluted when discrete washing and aspirating steps are employed. Also, the amount of fluid employed is independent of the volume of reaction vessel 17. Therefore, any amount of washing may be performed quickly and expeditiously. Because of the vacuum mode of operation, the entire test apparatus is closed preventing aerosolization and over-flow of reactants in case of operator carelessness.

In FIG. II, the apparatus 10 and reacton vessel 17 are the same as in FIG. I$a$, however, reaction zone 21 contains a single large bead having anti-HB$_s$ coated on the surface. Use of a single large bead obviates the need for fingers 29 and 31 (FIG. I$a$) to restrain the small beads 23. A test for hepatitis antigen using the single large bead of FIG. II and the apparatus of the invention is conducted as described above. A particular problem associated with the use of a single large bead is that the amount of antibody present on any bead may vary greatly. Using a number of small beads, the antibody level on individual beads may vary widely but the total amount of antibody remains relatively constant from one group of beads to the next. Also, it is possible to vary the amount of antibody present by merely adding or removing beads. For these reasons, it is preferred to use the apparatus of the invention with a number of small beads as depicted in FIG. I$a$.

The apparatus of the invention can be used in a number of different immunochemical tests. Use of the apparatus in hepatitis testing has been described. In addition, the apparatus is useful in any immunochemical test requiring one or more sequences of washing steps such as are carried out in tests based on the "sandwich" and "competition" principles. Exemplary uses of the apparatus involve sandwich tests for adenovirus, influenza virus, herpes virus, and $\alpha$-fetoprotein, and competition tests for drugs (digitoxin, morphine, digoxin), hormones, and a wide variety of specific antibodies. The reagents (i.e., antigens, antibodies or specific binding substances, depending upon the test to be conducted) are either adsorbed or covalently bound to a suitable supporting surface such as one or more beads or the interior surface of the reaction vessel.

The above tests are conducted using conventional reagents labelled with enzymes, radioisotopes, or florochromes (e.g. fluorescein).

In testing for HB$_s$Ag, the anti-HB$_s$ can be either adsorbed or covalently bound to the support surface. To adsorb the immuno-globulin supporting surface, a solution containing immuno-globulin with anti-HB$_s$ specificity, having a concentration of from 1 to about 100 micrograms of protein per ml. is prepared in from about 0.005 to about 0.02 molar Tris-HCl, i.e., 2-amino-2-hydroxymethyl-1,3-propanediol-HCl. The tris-HCl buffers the solution to a pH of from about 7.1 to about 9.5 along with from about 0.1% to about 0.5% sodium azide. One ml. of this solution is then contacted by the supported surface and incubated at room temperature for from 6 to 72 hours. The resultant immunoglobulin coated surface is then washed with about 0.005 to about 0.02 molar Tris-HCl at pH of 6.9 to 8.4 plus from about 0.01% to about 0.05% sodium azide. Following these washing and rinsing steps, a reaction vessel containing the supporting surface in the form of, for example, one or more beads may be stored at 4° C. until necessary for use.

To covalently bind anti-HB$_s$ immunoglobulin (or other antibodies) to a supporting surface such as polystyrene (in bead or latex form), the following procedure may be employed. Treatment with glacial acetic acid, fuming red nitric acid, and a solution of sodium hydroxide and sodium dithionite, in that order, converts the polystyrene beads into polyamino-styrene beads. Treatment with sodium nitrite and hydrochloric acid diazotizes the beads. The antibodies are added and the solution neutralized with sodium hydroxide. The tyrosine component of the antibody molecule forms covalent bonds with diazo groups on the bead surface bonding the antibody to the polystyrene. The beads may be stored wet at 4° C. or dry at room temperature.

What is claimed is:

1. Test apparatus for the performance of solid supported immunochemical reactions in diagnostic tests on samples of blood, serum, urine, and other liquids comprising:

a reaction vessel having an open end and a closed end, which vessel (1) is fitted with a fluid permeable grid member above the closed end defining a reaction chamber between the grid and the closed end to form a reaction zone and (2) has one or more geometrical solids within said chamber with immunochemical test reagents supported thereon, said chamber adapted to receive a washing apparatus, and (3) is adapted to receive the washing apparatus in vacuum sealing engagement; and a washing apparatus having a longitudinal axis and adapted for insertion (a) into the reaction vessel through the open end thereof to form a vacuum seal therewith, and (b) into the reaction chamber, comprising (1) a container to receive fluid, said container adapted to communicate with a source of fluid located externally to the reaction vessel, said container being fitted with a plurality of ports in a band, each port equidistant from another for continuously ejecting fluid from the container into the reaction vessel, and for washing the reaction vessel and the geometrical solids therein, and (2) an elongated vacuum conduit passing through the container in parallel to the longitudinal axis thereof, said conduit having a first vent adapted to communicate with a vacuum source and a second vent communicating with the interior of the reaction chamber to capture and remove fluid as said fluid is released from the container.

2. A test apparatus as in claim 1 wherein the immunochemical reagents are covalently bound to the geometrical solids.

3. A test apparatus as in claim 1 wherein the immunochemical test reagents are adsorbed onto the geometrical solids.

4. A test apparatus as in claim 1 wherein the reaction vessel is constructed of plastic.

5. A test apparatus as in claim 1 wherein the fluid container and vacuum conduit are cylindrical tubes having parallel, spaced-apart sides and a common axis, the vacuum conduit being positioned within and extending through the container said container having closed first and second end portions mating with the vacuum conduit.

6. A test apparatus as in claim 1 for performing diagnostics tests on human blood, serum, or plasma to detect hepatitis B surface antigen wherein the geometrial solids support an antibody specific against said hepatitis B surface antigen.

7. A test apparatus as in claim 6 wherein the geometrical solids for the hepatitis antibody are a plurality of beads.

8. A test apparatus as in claim 6 wherein the hepatitis antibody is covalently bound to the geometrical solids.

9. A test apparatus as in claim 6 wherein the heptatis antibody is adsorbed onto the geometrical solids.

10. A test apparatus as in claim 6 wherein the reaction vessel is constructed of clear plastic.

11. A method for washing samples of blood, urine, and other body fluids out of a reaction vessel containing said fluids during the performance of solid phase immunological reactions in diagnostic tests comprising the steps of:
   a. depositing said fluids into a reaction vessel having an open end and a closed end, which vessel (1) is fitted with a fluid permeable grid members above the closed end defining a reaction chamber between the grid and the closed end to form a reaction zone and (2) has one or more geometrical solids within said chamber with immunochemical test reagents supported thereon, said chamber adapted to receive a washing apparatus, and (3) is adapted to receive the washing apparatus in vacuum sealing engagement;
   b. inserting a washing apparatus into said vessel to mate in vacuum-tight engagement with said vessel, said washing apparatus having (1) a longitudinal axis and fitted with a container to receive fluid, said container in communication with a source of fluid located externally to the container, said container being fitted with a plurality of ports in a band, each port equidistant from another for continuously ejecting fluid from the container into the reaction vessel and for washing the reaction vessel and the geometrical solids therein, and (2) an elongated vacuum conduit passing through the container in parallel with the longitudinal axis of the container, said conduit having a first vent adapted to communicate with a vacuum source and a second vent communicating with the interior of the reaction chamber; and
   c. drawing through the vacuum conduit of the washing apparatus thereby ejecting fluid from the container into the reaction vessel and simultaneously capturing and removing said fluid through the vacuum conduit out of the reaction vessel.

12. A method as in claim 11 wherein the fluid tested is selected from the group consisting of blood, serum, and plasma and the test is for hepatitis B surface antigen.

13. A reaction vessel for diagnostic tests involving immmunochemical reactions with solid-supported reagents to detect antigens, antibodies and other etiological agents in samples of blood, serum, urine, and other liquids, having an open end, and a closed end, which vessel (1) is fitted with a fluid permeable grid member above the closed end defining a reaction chamber between the grid and the closed end to form a reaction zone and adapted to receive a washing apparatus and (2) has one or more geometrical solids within said chamber with test reagents supported on said solids.

14. The vessel recited in claim 13 wherein the geometrical solids comprise one or more beads.

15. The vessel recited in claim 13 wherein said vessel is so adapted to receive the washing apparatus in vacuum sealing engagement.

* * * * *